US011234709B2

(12) United States Patent
Hazama

(10) Patent No.: US 11,234,709 B2
(45) Date of Patent: Feb. 1, 2022

(54) HEMOSTATIC DEVICE

(71) Applicant: TERUMO KABUSHIKI KAISHA, Tokyo (JP)

(72) Inventor: Kenichi Hazama, Bear, DE (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 400 days.

(21) Appl. No.: 16/238,879

(22) Filed: Jan. 3, 2019

(65) Prior Publication Data
US 2019/0133606 A1    May 9, 2019

Related U.S. Application Data

(63) Continuation of application No. PCT/JP2017/024379, filed on Jul. 3, 2017.

(30) Foreign Application Priority Data

Jul. 6, 2016    (JP) .............................. JP2016-134600

(51) Int. Cl.
*A61B 17/135*    (2006.01)
*A61B 17/00*    (2006.01)
(Continued)

(52) U.S. Cl.
CPC .......... *A61B 17/135* (2013.01); *A61L 31/128* (2013.01); *A61L 31/143* (2013.01);
(Continued)

(58) Field of Classification Search
CPC ......................................... A61B 17/132–1355
See application file for complete search history.

(56) References Cited

U.S. PATENT DOCUMENTS

| 5,649,954 A * | 7/1997 | McEwen | A61B 17/135 |
| | | | 600/490 |
| 2002/0098341 A1* | 7/2002 | Schiffer | C08J 5/18 |
| | | | 428/323 |
| 2004/0098035 A1* | 5/2004 | Wada | A61B 17/1325 |
| | | | 606/201 |

FOREIGN PATENT DOCUMENTS

| JP | 2002309025 A | 10/2002 |
| JP | 2004201829 A | 7/2004 |

(Continued)

OTHER PUBLICATIONS

An English Translation of the International Search Report (Form PCT/ISA/210) and the Written Opinion of the International Searching Authority (Form PCT/ISA/237) dated Oct. 10, 2017, by the Japanese Patent Office in corresponding International Application No. PCT/JP2017/024379. (10 pages).

(Continued)

*Primary Examiner* — Elizabeth Houston
*Assistant Examiner* — Lindsey Bachman
(74) *Attorney, Agent, or Firm* — Buchanan Ingersoll & Rooney PC

(57) ABSTRACT

A hemostatic device is disclosed, which capable of favorably maintaining strength of an inflatable portion and reducing a pressing force acting on a site where bleeding is to be stopped over time to such an extent that vascular occlusion can be prevented without operation by a doctor or a nurse. The hemostatic device includes a band for wrapping around a wrist, a fastener or means for securing the band to the wrist in a wrapped state, and an inflatable portion connected to the band and inflated by being injected with a gas, in which the inflatable portion includes a resin layer made of a resin material, a particulate portion dispersed in the resin layer, and a space portion formed around the particulate portion. The space portion contains gas dispersed in the resin layer (Continued)

so as not to communicate between an inner surface and an outer surface of the resin layer.

21 Claims, 8 Drawing Sheets

(51) Int. Cl.
    *A61B 17/132*    (2006.01)
    *A61L 31/12*     (2006.01)
    *A61L 31/14*     (2006.01)
    *A61B 90/00*     (2016.01)

(52) U.S. Cl.
    CPC . *A61B 17/1325* (2013.01); *A61B 2017/00544* (2013.01); *A61B 2017/00557* (2013.01); *A61B 2017/00902* (2013.01); *A61B 2017/00955* (2013.01); *A61B 2090/0807* (2016.02); *A61B 2090/3937* (2016.02)

(56) References Cited

FOREIGN PATENT DOCUMENTS

| | | | |
|---|---|---|---|
| JP | 2008119517 A | 5/2008 | |
| JP | 2008188994 A | 8/2008 | |

OTHER PUBLICATIONS

International Search Report (PCT/ISA/210) dated Oct. 10, 2017, by the Japanese Patent Office as the International Searching Authority for International Application No. PCT/JP2017/024379.

* cited by examiner

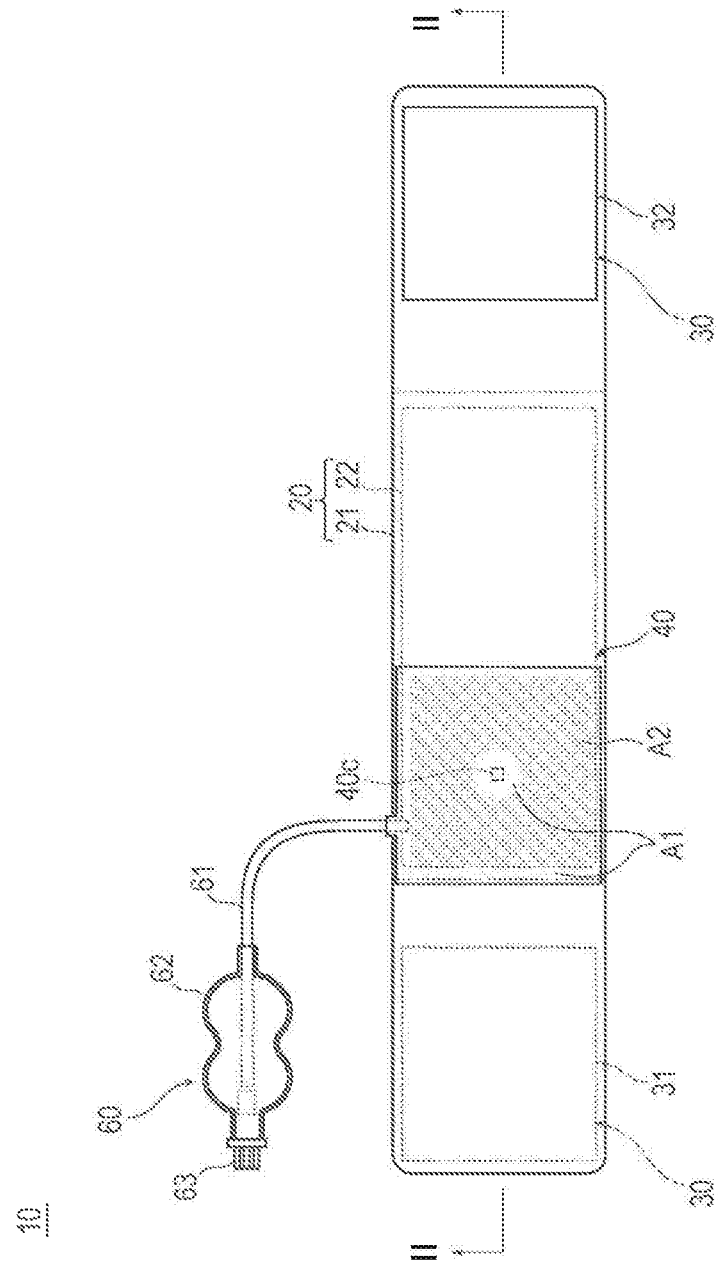

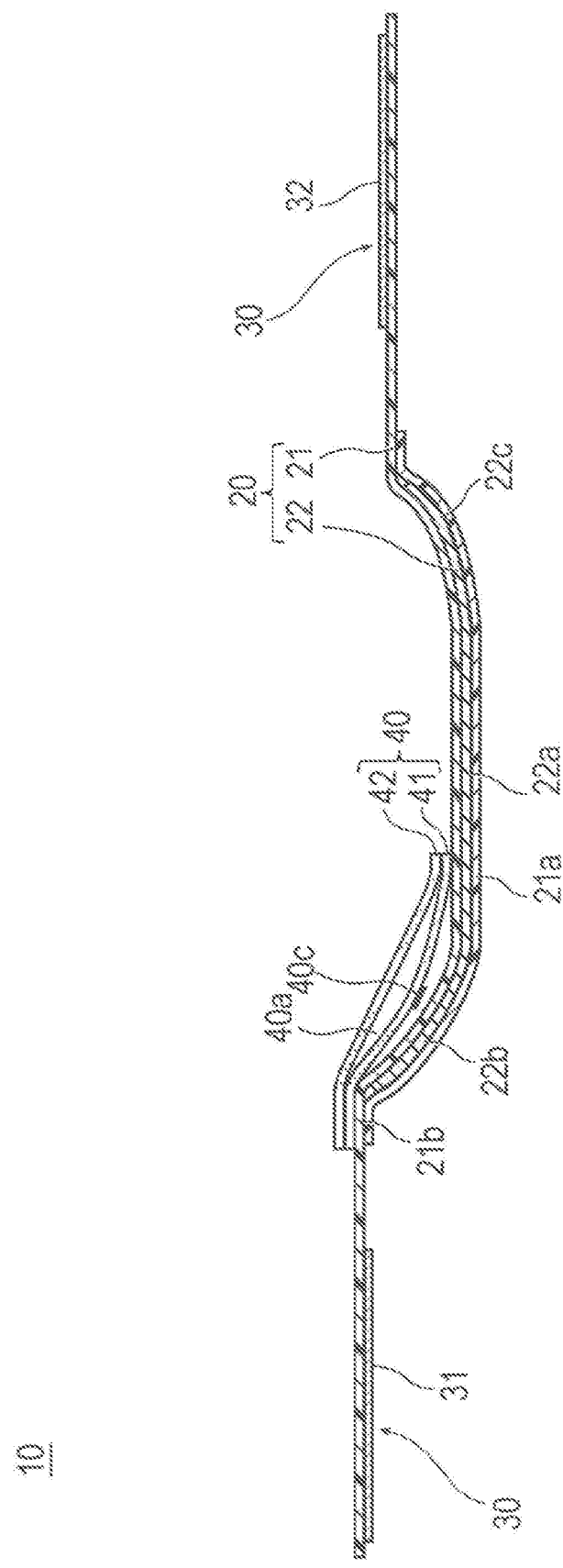

HEMOSTATIC DEVICE

CROSS-REFERENCES TO RELATED APPLICATIONS

This application is a continuation of International Application No. PCT/JP2017/024379 filed on Jul. 3, 2017, which claims priority to Japanese Application No. 2016-134600 filed on Jul. 6, 2016, the entire content of both of which is incorporated herein by reference.

TECHNICAL FIELD

The present disclosure generally relates to a hemostatic device for performing hemostasis by pressing a punctured site.

BACKGROUND DISCUSSION

Recently, percutaneous treatment/examination has been performed by puncturing a blood vessel of an arm or a leg, introducing an introducer sheath to a puncture site, and delivering a medical instrument such as a catheter to a lesion through a lumen of the introducer sheath. When such treatment/examination is performed, an operator needs to perform hemostasis in the puncture site after withdrawing the introducer sheath. To perform hemostasis, known hemostatic devices include a band for wrapping around a limb such as an arm or a leg, means for securing that secures the band in a state of being wrapping around the limb, and an inflatable portion connected to the band to press the puncture site by inflating in response to injection of a fluid into the inflatable portion.

In such a hemostatic device, when the inflating inflatable portion continues to strongly press the puncture site and a surrounding blood vessel or nerve for a relatively long time, there is a possibility of causing numbness, pain and/or occluding the blood vessel. In general, to prevent vascular occlusion, after inflating the inflatable portion, a doctor or a nurse regularly connects a dedicated instrument such as a syringe to the hemostatic device, discharges a fluid in the inflatable portion, and performs a depressurizing operation of depressurizing an internal pressure of the inflatable portion, which reduces a pressing force acting on the puncture site over time.

In a hemostatic device according to JP-A-2004-201829, an inflatable portion is made of a material that elongates over time. For this reason, after injecting a fluid into the inflatable portion, the inflatable portion is gradually inflated and transformed due to pressure from the fluid in the inflatable portion. Since the volume of an internal space of the inflatable portion gradually increases while the amount of the fluid in the inflatable portion is constant, the internal pressure of the inflatable portion can be reduced over time. In this way, it is possible to reduce the pressing force acting on the puncture site over time.

According to the hemostatic device according to JP-A-2004-201829, it is possible to save labor of performing the depressurizing operation by the doctor or the nurse. However, when the inflatable portion is made of the material that elongates (i.e., stretches) over time, the inflatable portion is inflated and transformed over time, and thus a thickness of the inflatable portion decreases accordingly. From a viewpoint of favorably maintaining the strength of the inflatable portion, it is considered preferable that the thickness of the inflatable portion be maintained to some extent.

SUMMARY

A hemostatic device is disclosed capable of favorably maintaining strength of an inflatable portion and reducing a pressing force acting on a site where bleeding is to be stopped over time to such an extent, that vascular occlusion can be prevented without operation by a doctor or a nurse.

A hemostatic device is disclosed that includes a band for wrapping around a site where bleeding is to be stopped of a limb, means for securing that secures the band to the limb in a wrapped state, and an inflatable portion connected to the band and inflated by being injected with gas, in which the inflatable portion includes a resin layer made of a resin material, a particulate portion dispersed in the resin layer, and a space portion formed around the particulate portion, and the space portion contains gas dispersed in the resin layer so as not to communicate between an inner surface of the resin layer and an outer surface of the resin layer.

A hemostatic device is disclosed comprising: a band configured to be wrapped around a site where bleeding is to be stopped of a limb; a fastener configured to secure the band to the limb in a wrapped state; and an inflatable portion configured to be connected to the band and inflated with an inflation gas, wherein the inflatable portion includes a resin layer made of a resin material, a particulate portion dispersed in the resin layer, and a space portion formed around the particulate portion, and the space portion formed around the particulate portion configured to receive a gas, and wherein the gas is dispersed in the resin layer so as not to communicate between an inner surface of the resin layer and an outer surface of the resin layer.

A hemostatic device is disclosed comprising: a band configured to be wrapped around a site where bleeding is to be stopped of a limb; a fastener configured to secure the band to the limb in a wrapped state; an inflatable portion configured to be connected to the band and inflated with an inflation gas, wherein the inflatable portion includes a resin layer made of a resin material, a plurality of particulate portions dispersed in the resin layer, and a space portion formed around each of the plurality of particulate portions, the space portion formed around each of the plurality of particulate portions being configured to receive a gas; and wherein the inflatable portion has a marker formed on the resin layer, and a distribution of the plurality of particulate portions in the resin layer at a position at which the marker is formed and around the marker is smaller than the distribution of the plurality of particulate portions in an other part of the resin layer.

A method is disclosed for performing hemostasis on a puncture site of a blood vessel of a patient's limb, the method comprising: wrapping a band of a hemostatic device around the patient's limb having the puncture site, the hemostatic device having an inflatable portion configured to be connected to the band and inflated with an inflation gas, wherein the inflatable portion includes a resin layer made of a resin material, a particulate portion dispersed in the resin layer, and a space portion formed around the particulate portion, and the space portion formed around the particulate portion configured to receive a gas, and wherein the gas is dispersed in the resin layer so as not to communicate between an inner surface of the resin layer and an outer surface of the resin layer; and securing the band to the patient's limb in a wrapped state.

According to the hemostatic device described above, the space portion contains gas and forms a free volume in which a gas molecule can freely move. For this reason, the inflatable portion has improved gas permeability when compared to a case in which the space portion is not included in the resin layer. Therefore, since the inflatable portion can control the gas permeation amount using the space portion in the resin layer, it is unnecessary to excessively decrease the thickness of the inflatable portion to increase the gas permeation amount. In addition, since the inflatable portion includes the particulate portion in the space portion, it is possible to increase the strength of the inflatable portion while suppressing deformation of the space portion. In this way, it is possible to reduce the pressing force acting on the site where bleeding is to be stopped over time without operation by a doctor or a nurse while favorably maintaining the strength of the inflatable portion.

BRIEF DESCRIPTION OF THE DRAWINGS

FIG. 1 is a plan view of a hemostatic device according to an embodiment viewed from an inner surface side.

FIG. 2 is a cross-sectional view taken along II-II line of FIG. 1.

FIGS. 3A-3C are plan views for description of an inflatable portion of the hemostatic device according to the embodiment, wherein FIG. 3A is a diagram illustrating a first sheet included in the inflatable portion, FIG. 3B is a diagram illustrating a second sheet included in the inflatable portion, and FIG. 3C is a plan view illustrating a connecting position of the inflatable portion and a band.

FIGS. 5A and 5B are cross-sectional views illustrating a state before the inflatable portion of the hemostatic device according to the embodiment is inflated, wherein FIG. 5A is a cross-sectional view taken along IV-IV line of FIG. 4, and FIG. 5B is an enlarged cross-sectional view of a part VB illustrated in FIG. 5A.

FIGS. 6A and 6B are cross-sectional views illustrating a state in which the inflatable portion of the hemostatic device according to the embodiment is inflated, wherein FIG. 6A is a cross-sectional view taken along IV-IV line of FIG. 4, and FIG. 6B is an enlarged cross-sectional view of a part VIB illustrated in FIG. 6A.

DETAILED DESCRIPTION

Figure 3A:
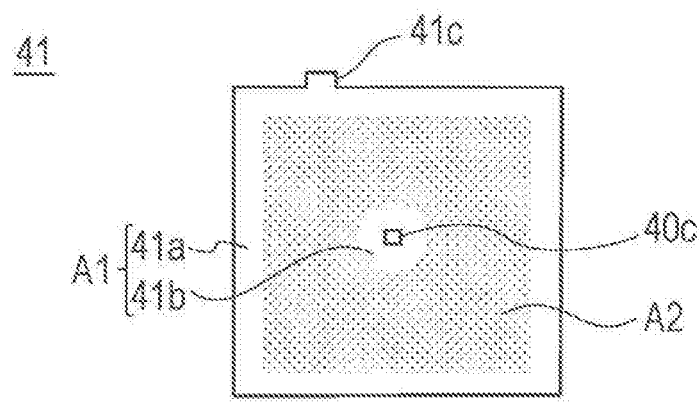

Hereinafter, an embodiment and modifications of the disclosure will be described with reference to accompanying drawings. Note that a description below does not restrict a technical scope or a meaning of a term described in claims. In addition, a ratio of dimensions in the drawings is exaggerated for convenience of description and may be different from an actual ratio.

Figure 4:
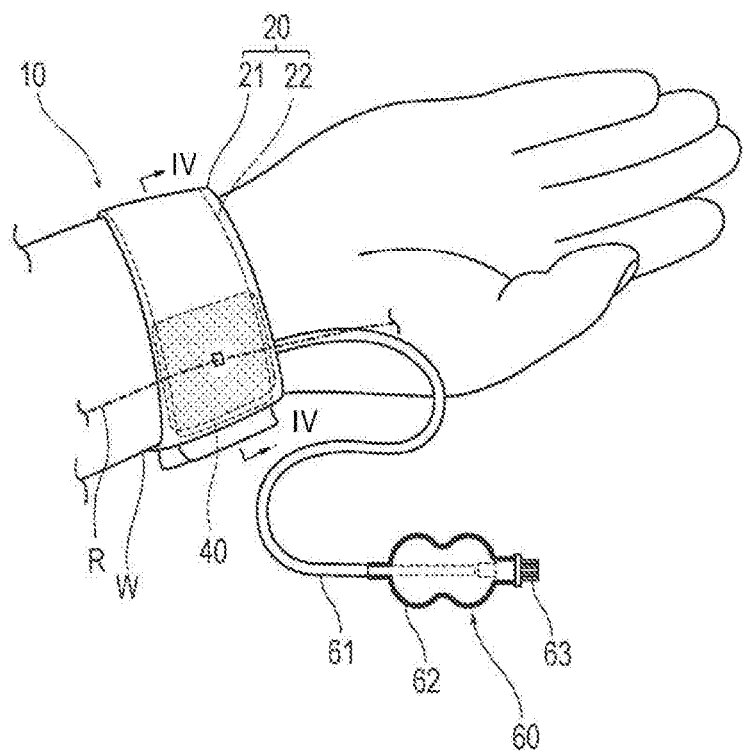
FIG. 4 is a perspective view illustrating a state in which the hemostatic device according to the embodiment is mounted on a wrist.
Figure 5A:
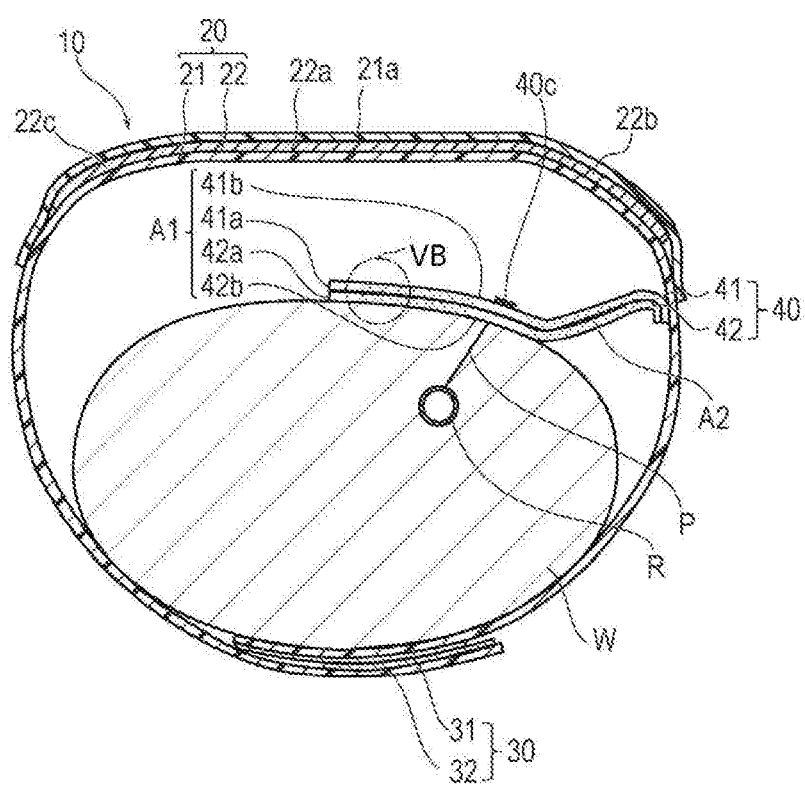

As illustrated in FIG. 4 and FIG. 5A, to insert a catheter, for example, for performing treatment/examination, into a blood vessel, after withdrawing an introducer sheath indwelled in a puncture site P (corresponding to a "site where bleeding is to be stopped") formed in a radial artery R of a wrist W (corresponding to a "limb"), a hemostatic device 10 according to the embodiment is used to stop bleeding in the puncture site P.

As illustrated in FIGS. 1 and 2, the hemostatic device 10 can include a band 20 for wrapping around the wrist W, a surface fastener 30 (corresponding to "means for securing" (securing member)) that secures the band 20 in a state of being wrapped around the wrist W, an inflatable portion 40 that inflates by being injected with a gas and presses the puncture site P, a marker 40c for positioning the inflatable portion 40 in the puncture site P, and an injection part 60 capable of injecting gas into the inflatable portion 40.

In the present disclosure, when the band 20 is wrapped around the wrist W, a side (mounting surface side) of the band 20 facing a body surface of the wrist W is referred to as an "inner surface side", and an opposite side is referred to as an "outer surface side".

The band 20 can include a belt 21 made of a belt-shaped member having flexibility and a support plate 22 having a higher rigidity than that of the belt 21.

As illustrated in FIGS. 4 and 5A, the belt 21 is wrapped around an outer periphery of the wrist W substantially once. As illustrated in FIG. 2, a support plate holding portion 21a that holds the support plate 22 is formed at a central portion of the belt 21. The support plate holding portion 21a can be doubled by separate belt-shaped members joined to an outer surface side (or inner surface side) of the support plate 22 using a method such as welding (heat-welding, high-frequency welding, ultrasound welding) or adhesion (adhesion by an adhesive or a solvent) and holds the support plate 22 inserted into a gap between the separate belt-shaped members of the support plate holding portion 21.

A male side (or a female side) 31 of the surface fastener 30 is disposed on the outer surface side of the belt 21 near a left end of FIG. 1, and a female side (or a male side) 32 of the surface fastener 30 is disposed on the inner surface side of the belt 21 near a right end of FIG. 1. For example, the surface fastener 30 is a hook and loop fastener known as a general product such as VELCRO ® or Magic tape ® in Japan. As illustrated in FIG. 4, the belt 21 is wrapped around the wrist W, and the male side 31 and the female side 32 are joined together, thereby mounting the band 20 on the wrist W. Note that means for securing the band 20 to the wrist W in a wrapped state is not limited to the surface fastener 30. For example, the means for securing the band 30 may correspond to a securing member such as a snap, a button, a clip, or a frame member passing an end portion of the belt 21.

In accordance with an exemplary embodiment, it can be preferable that the belt 21 is made of a resin material capable of connecting a first region A1 of the inflatable portion 40 described below using welding. In the belt 21, it is sufficient that a connecting region 21b (in the present embodiment, as illustrated in FIG. 2, a region between a region in which a first curved portion 22b of the support plate 22 described below is disposed and a region in which the male side 31 of the surface fastener 30 is attached) to which at least the inflatable portion 40 is connected is made of a resin material that can be welded to the inflatable portion 40, and a part other than the connecting region 21b may be formed of a material other than the resin material that can be welded to the inflatable portion 40.

Note that a connecting mode of the band 20 and the inflatable portion 40 is not particularly limited. For example, as in the present embodiment, the band 20 and the inflatable portion 40 may be directly secured (connected) to each other. Alternatively, for example, a tube 61 of the injection part 60 may be secured to the band 20, and the tube 61 and the inflatable portion 40 may be secured to each other, thereby connecting the inflatable portion 40 to the band 20 through the tube 61.

The belt 21 material is not particularly limited as long as the material has flexibility. Examples of such a material include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicone, polyurethane, various thermoplastic elastomers such as polyamide elastomers, polyurethane elastomers and polyester elastomers, and an arbitrary combination of the above (blend resin, polymer alloy, laminate, etc.).

For example, a thermoplastic material can be used as the material of the belt 21. As for the thermoplastic material, for example, it is possible to use a thermoplastic resin such as polyvinyl chloride, polyethylene, polypropylene, or polyvinylidene chloride or various thermoplastic elastomers such as an olefinic thermoplastic elastomer and a styrene thermoplastic elastomer. When the belt 21 is formed using a thermoplastic material, it becomes difficult to stretch the belt 21, and a state in which the inflatable portion 40 is pressed against the wrist W can be favorably maintained without being influenced, for example, by a size, etc. of the wrist W of the wearer. In addition, when the first region A1 of the inflatable portion 40 described below is formed of a thermoplastic material, the inflatable portion 40 may be connected to the belt, for example, by a weld (i.e., welding).

In accordance with an exemplary embodiment, at least a part of the belt 21 overlapping with the inflatable portion 40 is preferably substantially transparent. However, the overlapping part may not be transparent, and may be translucent or colored transparent. In this way, the puncture site P may be visually recognized from the outer surface side, and the marker 40c described below may be relatively easily positioned in the puncture site P.

As illustrated in FIG. 2, the support plate 22 is held in the belt 21 by being inserted into the doubly formed support plate holding portion 21a of the belt 21. At least a part of the support plate 22 has a plate shape curved toward the inner surface side (mounting surface side). The support plate 22 is made of a material that is more rigid than that of the belt 21 and is designed to maintain a substantially constant shape. However, a method of disposing the support plate 22 on the belt 21 is not limited to an illustrated configuration, and it is possible to include joining the support plate 22 to the inner surface or the outer surface of the band 20 using an appropriate method such as welding or adhesion. Similarly, another acceptable configuration is a configuration in which the belt 21 is connected to both end portions of the support plate 22. For this reason, it is not indispensable that the entire support plate 22 overlaps the belt 21.

In accordance with an exemplary embodiment, the support plate 22 has a shape elongated in a longitudinal direction of the belt 21. A central portion 22a in a longitudinal direction of the support plate 22 is formed in a flat plate shape with relatively little curvature. In accordance with an exemplary embodiment, a first curved portion 22b (left side of FIG. 2) and a second curved portion 22c (right side of FIG. 2) curved toward the inner surface side and along the longitudinal direction of the belt 21 (circumferential direction of the wrist W) are formed on both sides of the central portion 22a, respectively.

The support plate 22 material can include acrylic resins, polyvinyl chloride (particularly rigid polyvinyl chloride), polyolefins such as polyethylene, polypropylene and polybutadiene, polystyrene, poly(4-methyl pentene-1), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic or aliphatic polyamides, and fluorocarbon resins such as polytetrafluoroethylene.

In accordance with an exemplary embodiment, it can be preferable that a part of the support plate 22 overlapping the inflatable portion 40 is substantially transparent similarly to the belt 21. However, the part of the support plate 22 overlapping the inflatable portion 40 may not be transparent, and may be translucent or colored transparent. In this way, the puncture site P may be reliably visually recognized from the outer surface side, and the marker 40c described below may be rather easily positioned in the puncture site P. Note that the support plate 22 may not have a flat plate-shaped portion as the central portion 22a, and may be curved over an entire length of the support plate 22.

The inflatable portion 40 has a function of inflating by being injected with a gas to apply a pressing force to the puncture site P and a function of reducing the pressing force applied to the puncture site P over time by discharging the injected gas to the outside over time. Note that the gas injected into the inflatable portion 40 is not particularly limited as long as the inflatable portion 40 can be inflated. For example, the gas can be air.

Figure 5B:
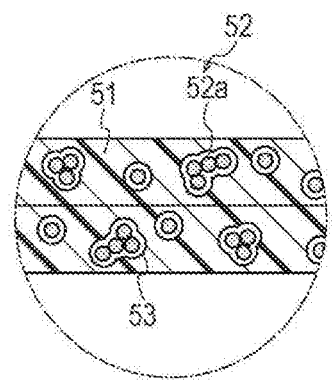

As illustrated in FIG. 5B, the inflatable portion 40 includes a resin layer 51 made of a resin material, a particulate portion 52 dispersed in the resin layer 51, and a space portion 53 formed around the particulate portion 52. In addition, the inflatable portion 40 has the marker 40c for positioning the inflatable portion 40 in the puncture site P (see FIG. 1).

The resin layer 51 material is not particularly limited as long as the material has flexibility. For example, the resin layer material can be the same material as the material of the belt 21. In addition, it is preferable that the inflatable portion 40 is made of a thermoplastic material which is the same material as or a similar to the material of the belt 21. In this way, it is possible to rather easily join the inflatable portion 40 to the band 20 using welding, and to rather easily manufacture the hemostatic device 10.

The resin layer 51 is preferably substantially transparent. However, the resin layer 51 may not be transparent, and may be translucent or colored transparent.

As illustrated in FIG. 5B, the particulate portion 52 has a substantially spherical shape and includes one or a plurality of particles 52a. When the particulate portion 52 includes the plurality of particles 52a, the particles 52a may be dispersed or in contact with each other by aggregation, for example, due to an intermolecular force. When the plurality of particles 52a is aggregated, since each of the particles 52a has a substantially spherical shape, a gap is formed between adjacent particles 52a. When a gap is included in this way, gas can flow between the adjacent particles 52a, and thus gas permeability in the particulate portion 52 can be improved.

Note that a position at which the particulate portion 52 is formed in the resin layer 51, the number of particles 52a in the particulate portion 52, internal diameters of the space portion 53 and the particulate portion 52, are not particularly limited as long as gas can be discharged from the inflatable portion 40.

The material of the particles 52a, for example, in accordance with an exemplary embodiment, is preferably a known metallic material such as silicon, aluminum, copper, stainless steel, iron, or an alloy obtained by mixing a predetermined two or more types of metals. According to the metallic material, an electrostatic repulsive force for repelling and dispersing the particles 52a can be relatively easily formed. However, the material of the particles 52a may be any material that can be at least dispersed by utilizing the electrostatic repulsive force, between the particles 52a when the particulate portion 52 is formed in the resin layer 51. Therefore, the material of the particles 52a is not limited to the metallic material. For example, the material of the particles 52a can be aluminosilicate, ceramic such as alumina or silica, a resin material such as thermosetting elastomer, polymer such as latex, glass, etc. Note that a method of dispersing the particulate portion 52 is not limited to a configuration utilizing the electrostatic repulsive force, and the particles 52a may be physically dispersed by ultrasound waves, for example, when the particulate portion 52 is formed in the resin layer 51.

In accordance with an exemplary embodiment, the space portion 53 contains gas dispersed in the resin layer 51 so as not to communicate (i.e., the space portion is not fluidly connected) between an inner surface of the resin layer 51 and an outer surface of the resin layer 51. In accordance with an exemplary embodiment, the space portion 53 may not be disposed to surround the entire periphery of the particulate portion 52, and may be, for example, disposed to surround a partial range around the particulate portion 52. When the space portion 53 is disposed in this way, a part of the particulate portion 52 is in contact with the resin layer 51.

Figure 6A:
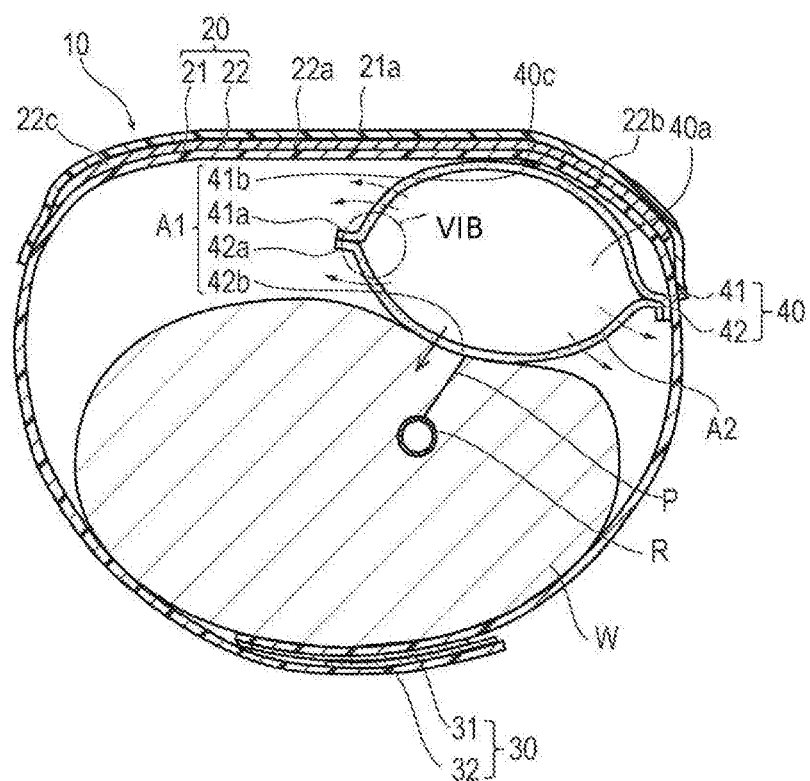
Figure 6B:
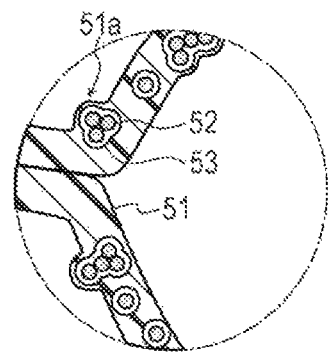

As illustrated in FIGS. 6A and 6B, in a state in which the inflatable portion 40 inflates, a thickness of the resin layer 51 decreases. In addition, the space portion 53 maintains a volume of the space portion 53 in the state in which the inflatable portion 40 inflates. For this reason, as illustrated in FIG. 6B, in the state in which the inflatable portion 40 inflates, the outer surface of the resin layer 51 is pushed from the inside of the resin layer 51 and protrudes by the particulate portion 52 and the space portion 53. That is, a part of the particulate portion 52 and the space portion 53 pushes out the outer surface of the resin layer 51 from the inside of the resin layer 51 so that the outer surface of the resin layer 51 protrudes. This protruding portion forms an uneven portion 51a on a part of an outer surface of the inflatable portion 40. When the uneven portion 51a is formed on the outer surface of the inflatable portion 40, a contact area between the surface of the inflatable portion 40 and the wrist W increases, so that a frictional force between the surface of the inflatable portion 40 and the wrist W increases. In this way, it is possible to favorably press the puncture site P by preventing shift of the inflatable portion 40 with respect to the puncture site P.

Note that a diameter of the particle 52a of the particulate portion 52 is not particularly limited as long as dispersion in the resin layer 51 of the first sheet 41 and the second sheet 42 is allowed and the uneven portion 51a can be formed on a part of the surface of the inflatable portion 40 in the state in which the inflatable portion 40 inflates. For example, the diameter of the particles 52a of the particulate portion 52 can be 1 μm to 200 μm, more preferably 1 μm to 10 μm.

As illustrated in FIGS. 1 and 2, the inflatable portion 40 is formed by superposing the first sheet 41 and the second sheet 42 on one another to form a bag shape. As illustrated in FIG. 2, an inflatable space 40a into which gas can be injected is formed inside the inflatable portion 40.

Figure 3B:
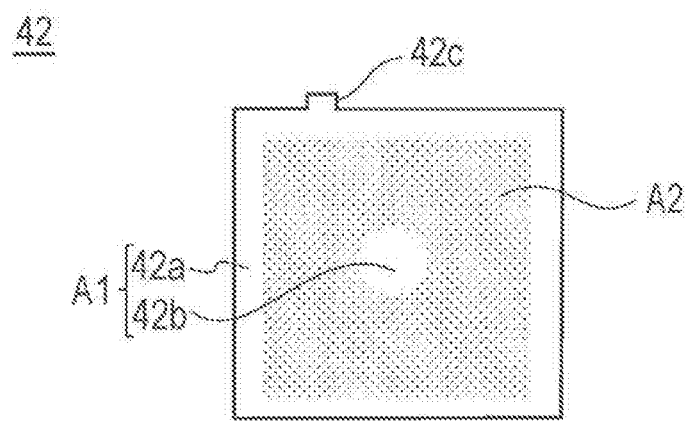
Figure 3C:
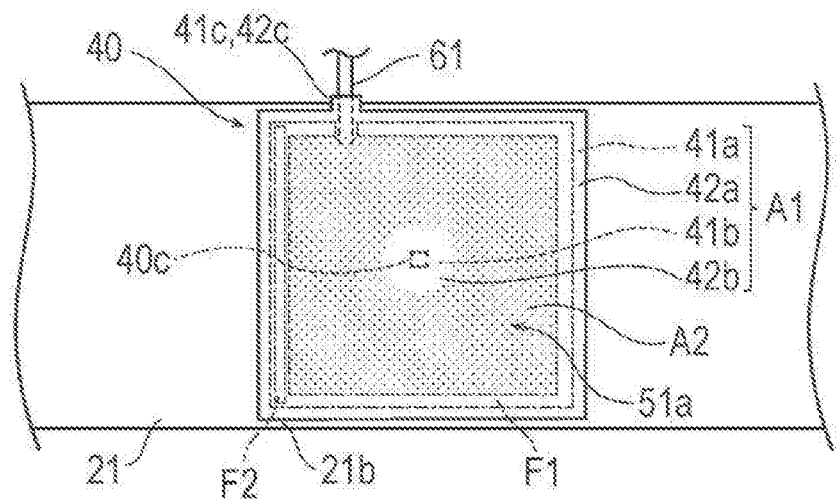

FIG. 3A illustrates the first sheet 41 in a state before the inflatable portion 40 is formed, FIG. 3B illustrates the second sheet 42 in the state before the inflatable portion 40 is formed, and FIG. 3C illustrates a state in which the inflatable portion 40 including the respective sheets 41 and 42 is connected to the belt 21 of the band 20.

In accordance with an exemplary embodiment, the first sheet 41 has a substantially rectangular external shape in plan view illustrated in FIG. 3A. A protrusion 41c protruding outward from a rectangular portion is provided on the first sheet 41.

The second sheet 42 has a substantially rectangular external shape in plan view illustrated in FIG. 3B. A protrusion 42c protruding outward from a rectangular portion is provided on the second sheet 42. In addition, the marker 40c is provided at a substantially central portion of the second sheet 42 in plan view.

As illustrated in FIG. 3C, the tube 61 of the injection part 60 described below is disposed between the protrusion 41c of the first sheet 41 and the protrusion 42c of the second sheet 42. Further, the respective protrusions 41c and 42c are attached to the tube 61 by an adhesive. In this way, the tube 61 can be held by the inflatable portion 40. Note that the external shapes of the first sheet 41 and the second sheet 42 are not particularly limited to the above shape, and may correspond to, for example, a circle, an ellipse, or a polygon. In addition, the protrusions 41c and 42c may not be provided.

As illustrated in FIG. 3A, in a central portion 41b and a peripheral portion 41a of the first sheet 41, the first sheet 41 is formed such that a distribution of the particulate portion 52 and the space portion 53 in the resin layer 51, that is, a volume fraction of the particulate portion 52 and the space portion 53 in the resin layer 51 is smaller than that of the other part of the resin layer 51.

Similarly, as illustrated in FIG. 3B, in a central portion 42b and a peripheral portion 42a of the second sheet 42, the second sheet 42 is formed such that the distribution of the particulate portion 52 and the space portion 53 in the resin layer 51, that is, the volume fraction of the particulate portion 52 and the space portion 53 in the resin layer 51 is smaller than that of the other part of the resin layer 51.

The first region A1 of the inflatable portion 40 includes a region in which the distribution of the particulate portion 52 and the space portion 53 in the resin layer 51 is relatively small. In other words, in the inflatable portion 40, the peripheral portion 41a of the first sheet 41, the peripheral portion 42a of the second sheet 42, the central portion 41b of the first sheet 41, and the central portion 42b of the second sheet 42 correspond to the first region A1.

A second region A2 of the inflatable portion 40 is a region in which the distribution of the particulate portion 52 and the space portion 53 in the resin layer 51 is larger than that of the first region A1.

As illustrated in FIG. 3C, the marker 40c described below is provided at the central portion 41b of the first sheet 41. In addition, in a state in which the first sheet 41 and the second sheet 42 are superposed on one another, the central portion 41b of the first sheet 41 is disposed to face the central portion 42b of the second sheet 42. In other words, a position at which the marker 40c is formed and a periphery of the marker 40c are disposed in the first region A1. In the first region A1, the volume fraction of the particulate portion 52 is relatively small, and thus visibility is hardly interrupted by the particulate portion 52. For this reason, it is possible to visually recognize the puncture site P from the outer surface side, and to rather easily position the marker 40c in the puncture site P.

In addition, as illustrated in FIG. 3C, the peripheral portion 41a of the first sheet 41 and the peripheral portion 42a of the second sheet 42 are joined by a first joining portion F1 in the state in which the first sheet 41 and the second sheet 42 are superposed on one another. In other words, the first joining portion F1 is disposed in the first region A1.

In addition, as illustrated in FIG. 3C, one side of the peripheral portion 41a of the first sheet 41 and an inner surface side of the connecting region 21b of the band 20 are joined by a second joining portion F2. In other words, the second joining portion F2 is disposed in the first region A1. Note that joining in the first joining portion F1 and the second joining portion F2 may be performed by, for example, a method such as welding or adhesion using an adhesive.

As described above, since the first joining portion F1 and the second joining portion F2 are disposed in the first region A1 in which the volume fraction of the particulate portion 52 and the space portion 53 is relatively small, the thickness of the resin layer 51 is thicker than that of the second region A2. For this reason, it is possible to suppress a decrease in strength of a joining part due to a decrease in thickness of the resin layer 51.

Note that in a case of joining the second joining portion F2 by welding, it is possible to increase bonding strength between the first sheet 41 and the band 20 by setting a resin material used for the resin layer 51 of the first sheet 41 and a resin material used for the connecting region 21b of the band 20 to the same thermoplastic material and performing welding in the second joining portion F2. However, the resin material used for the first sheet 41 and the resin material used for the connecting region 21b of the band 20 may be different from each other. Similarly, in a case of joining the first joining portion F1 by welding, it is possible to increase bonding strength between the first sheet 41 and the second sheet 42 in the first joining portion F1 by setting a resin material used for the first sheet 41 and a resin material used for the second sheet 42 to the same thermoplastic material. However, the resin material used for the first sheet 41 and the resin material used for the second sheet 42 may be different from each other.

In the resin layer 51 of the inflatable portion 40, gas permeation based on a gas dissolution/diffusion phenomenon occurs. In accordance with an exemplary embodiment, a gas permeation coefficient is inversely proportional to a thickness of a region to be transmitted (a distance in which a gas molecule moves). Here, the second region A2 is formed such that a volume fraction of the space portion 53 is higher than that of the first region A1. The space portion 53 contains a gas and forms a free volume in which a gas molecule can freely move. When comparison is performed using the resin layer 51 having the same thickness, a theoretical thickness contributing to the gas permeation coefficient is smaller in a case in which the space portion 53 is included in the resin layer 51 than in a case in which the space portion 53 is not included in the resin layer 51. For this reason, a gas permeation amount per unit area in the second region A2 is larger than that in the first region A1. In this way, it is possible to discharge gas in the inflatable portion 40 through the second region A2 over time in the state in which the inflatable portion 40 inflates. In addition, since it is unnecessary to reduce the thickness of the inflatable portion 40 to improve gas permeability, the strength of the inflatable portion 40 can be maintained.

Note that in the first region A1, the gas is discharged to the outside of the inflatable portion 40 over time due to a dissolution/diffusion phenomenon of gas. For this reason, to facilitate adjustment of a discharge amount of gas while making discharge of gas in the second region A2 dominant, a gas permeation amount per unit area in the second region A2, for example, is preferably 10 times or more of a gas permeation amount per unit area in the first region A1, more preferably 100 times or more, still more preferably 1,000 times or more. In this way, the hemostatic device 10 may suitably adjust a decrease of a pressing force applied to the puncture site P of the inflatable portion 40 over time by a difference in gas permeation amount per unit area between the first region A1 and the second region A2.

It is preferable that the second region A2 is formed to realize a depressurization protocol satisfying the following Conditions 1 and 2.

(Condition 1) When gas is discharged to the outside of the inflatable portion 40 through the second region A2 over four hours after inflation in a state in which the band 20 is wrapped around the wrist W, an internal pressure of the inflatable portion 40 at every lapse of one hour is 70 to 97% (preferably 75 to 94%) of an internal pressure of the inflatable portion 40 before one hour; and (Condition 2) An internal pressure in the inflatable portion 40 after four hours elapse after inflation in the state in which the band 20 is wrapped around the wrist W is 30 to 80% (preferably 40 to 71%) of an initial internal pressure.

The volume of the space portion 53 may be formed to be able to realize the depressurization protocol described above depending on the number of space portions 53 provided in the second region A2, the thickness of the second region A2, the quality of the material forming the second region A2, and the use condition at the time of using the hemostatic device 10 (pressure difference between the inside and the outside of the inflatable portion 40 during hemostasis). Note that when a plurality of space portions 53 is formed in the second region A2 as in the present embodiment, it is possible to adjust a discharge amount of gas in the second region A2 by adjusting arrangement (distribution) of the space portions 53.

As illustrated in FIG. 6A, the inflatable portion 40 is disposed on the inner surface side of the band 20. For this reason, when the inflatable portion 40 is inflated, inflation of the inflatable portion 40 in a direction away from the body surface of the wrist W is suppressed by the band 20. In this way, a pressing force of the inflatable portion 40 is concentrated on the wrist W side, and the pressing force can be suitably applied to the puncture site P. In addition, since the inflatable portion 40 is pressed against the wrist W by the band 20 to increase the internal pressure, it is possible to suitably discharge gas in the inflatable portion 40 to the outside.

In addition, as illustrated in FIG. 6A, the inflatable portion 40 is disposed at a position overlapping the first curved portion 22b of the support plate 22. For this reason, when the inflatable portion 40 is inflated, inflation of the inflatable portion 40 in the direction away from the body surface of the wrist W is suppressed by the support plate 22, and the pressing force of the inflatable portion 40 is concentrated on the wrist W side. Since the pressing force can be concentrated on the puncture site P by the support plate 22, hemostasis can be suitably performed in the puncture site P.

As illustrated in FIG. 2, the marker 40c is provided at an approximate center on the outer surface side disposed on the band 20 side (approximate center of the first sheet 41) in the inflatable portion 40. When such a marker 40c is provided in the inflatable portion 40, the inflatable portion 40 can be rather easily positioned with respect to the puncture site P, and thus position shift of the inflatable portion 40 is suppressed. In addition, since the marker 40c is provided on the band 20 side of the inflatable portion 40, the marker 40c does not directly come into contact with the puncture site P. Note that a position at which the marker 40c is provided is not particularly limited as long as the inflatable portion 40 may be positioned in the puncture site P. For example, the marker 40c may be provided at an approximate center on the outer surface side disposed on the wrist W side (approximate center of the second sheet 42) on the inner surface of the inflatable portion 40.

A shape of the marker 40c is not particularly limited, and examples of the shape of the marker 40c can include a circle, a triangle, a quadrangle, etc. In present embodiment, the shape of the marker 40c corresponds to the quadrangle.

A size of the marker 40c is not particularly limited. For example, when the shape of the marker 40c corresponds to the quadrangle, it is preferable that a length of one side of quadrangle is in a range of 1 mm to 4 mm. When the length of the one side of the quadrangle is 5 mm or more, the size of the marker 40c increases with respect to a size of the puncture site P, and thus it can be difficult to position a central portion of the inflatable portion 40 in the puncture site P.

The marker 40c material is not particularly limited. Examples of the marker 40c material can include an oily coloring agent such as ink, or a resin kneaded with a pigment.

A color of the marker 40c is not particularly limited when the color allows the inflatable portion 40 to be positioned in the puncture site P. However, a green-based color can be preferable for the color of the marker 40c. When the green-based color is adopted, the marker 40c can be visually recognized on blood or skin, and thus the inflatable portion 40 is more easily positioned in the puncture site P.

In addition, the marker 40c is preferably translucent or colored transparent. In this way, the puncture site P may be visually recognized from the outer surface side of the marker 40c.

A method of providing the marker 40c on the inflatable portion 40 is not particularly limited. Examples of the marker 40c method can include printing the marker 40c on the inflatable portion 40, and applying an adhesive to one surface of the marker 40c to paste the marker 40c to the inflatable portion 40.

The injection part 60 corresponds to a site for injecting gas into the inflatable portion 40, and is connected to the inflatable portion 40 as illustrated in FIG. 1.

The injection part 60 is a tube 61 having flexibility, a proximal portion of the tube 61 is connected to the inflatable portion 40 and a lumen of the tube 61 communicates with the inside of the inflatable portion 40, a bag body 62 disposed at a distal portion of the tube 61 to communicate with a lumen of the tube 61, and a tube-shaped connector 63 incorporating a check valve (not illustrated) connected to the bag body 62.

As illustrated in FIG. 3C, the tube 61 is connected to the inflatable portion 40 such that the tube 61 is interposed between the protrusion 41c of the first sheet 41 and the protrusion 42c of the second sheet 42. However, a position at which the tube 61 is connected in the inflatable portion 40 is not particularly limited as long as the lumen of the tube 61 communicates with the inflatable space 40a of the inflatable portion 40.

At the time of inflating (expanding) the inflatable portion 40, a tip of a syringe (not illustrated) is inserted into the connector 63 to open a check valve, and a plunger of this syringe is pushed to inject gas in the syringe into the inflatable portion 40 through the injection part 60. When the inflatable portion 40 inflates, the bag body 62 communicating with the inflatable portion 40 through the tube 61 also inflates, and it is possible to visually confirm that the inflatable portion 40 can be pressed without leakage of gas. When the tip of the syringe is withdrawn from the connector 63 after gas is injected into the inflatable portion 40, the check valve incorporated in the connector 63 is closed to prevent leakage of gas.

Next, a description will be given of a method of using the hemostatic device 10 according to the present embodiment.

Before the hemostatic device 10 is mounted on the wrist W, as illustrated in FIG. 2, the inflatable portion 40 is in a state of not being inflated. As illustrated in FIGS. 4, 5A, and 6A, when the radial artery R of the right hand wrist W is punctured, the puncture site P is at a position biased to a thumb side. Normally, the introducer sheath is indwelled in the puncture site P. The band 20 is wrapped around the wrist W in which the introducer sheath is indwelled, the inflatable portion 40 and the band 20 are positioned such that the marker 40c provided on the inflatable portion 40 overlaps the puncture site P, and the male side 31 and the female side 32 of the surface fastener 30 are brought into contact with each other and joined to each other, thereby mounting the band 20 on the wrist W.

In this instance, the hemostatic device 10 is mounted on the wrist W such that the injection part 60 faces a downstream side (palm side) of a blood flow of the radial artery R. In this way, the injection part 60 may be operated without interfering with manipulation on the upstream side of the wrist or a device (for example, a sphygmomanometer, i.e., an instrument for measuring blood pressure) located on the upstream side. In addition, when the hemostatic device 10 is mounted on the right hand wrist W such that the injection part 60 faces the downstream side, the inflatable portion 40 is located on the radial artery R biased to the thumb side of the wrist W. Note that in the case of the artery, the upstream side (i.e. proximal side) of the blood vessel refers to a direction of the blood vessel approaching a heart. In addition, the downstream side (i.e., distal side) of the blood vessel refers to a direction of the blood vessel away from the heart.

Note that the hemostatic device 10 may be used for puncturing the radial artery of the left hand wrist. In this case, the injection part 60 is mounted on the left hand wrist to face the upstream side of the blood flow of the radial artery.

After the hemostatic device 10 is mounted on the wrist W, the syringe (not illustrated) is connected to a connector 63 of the injection part 60, gas is injected into the inflatable portion 40 as described above, and the inflatable portion 40 is inflated.

A degree of inflation of the inflatable portion 40, that is, a pressing force acting on the puncture site P may be easily adjusted depending on the case according to an injection amount of gas at this time. For example, when gas is excessively injected into the inflatable portion 40, and thus the inflatable portion 40 excessively inflates, surplus gas may be discharged from the inside of the inflatable portion 40 using a syringe.

After the inflatable portion 40 is inflated, the syringe is detached from the connector 63. Then, the introducer sheath is withdrawn from the puncture site P.

After the inflatable portion 40 is inflated, while a pressing force is applied to the puncture site P, gas in the inflatable portion 40 is discharged to the outside of the inflatable portion 40 through the second region A2 over time to such an extent that vascular occlusion can be prevented.

Note that when hemostasis is not sufficiently performed after inflation of the inflatable portion 40, gas may be injected into the inflatable portion 40 to raise the internal pressure of the inflatable portion 40. For example, when it is desirable to return the internal pressure of the inflatable portion 40 to the internal pressure at the time of injecting gas into the inflatable portion 40, gas discharged from the inflatable portion 40 may be injected.

When a predetermined time elapses, and hemostasis of the puncture site P is completed, the hemostatic device 10 is removed from the wrist W. The hemostatic device 10 is removed from the wrist W by peeling off the male side 31 and the female side 32 of the surface fastener 30.

As described above, the hemostatic device 10 according to the present embodiment includes the band 20 for wrapping around the puncture site P of the wrist W, the means for securing 30 that secures the band 20 in the state of being wrapped around the wrist W, and the inflatable portion 40 which is connected to the band 20, inflates by being injected with gas, and presses the puncture site P. The inflatable portion 40 includes the resin layer 51 made of the resin material, the particulate portion 52 dispersed in the resin layer 51, and the space portion 53 formed around the particulate portion 52. The space portion 53 contains gas dispersed in the resin layer 51 so as not to communicate between the inner surface of the resin layer 51 and the outer surface of the resin layer 51.

According to the hemostatic device 10 configured as described above, the space portion 53 contains gas and forms a free volume in which a gas molecule can freely move. For this reason, the inflatable portion 40 has improved gas permeability when compared to a case in which the space portion 53 is not included in the resin layer 51. Therefore, since the inflatable portion 40 can control the gas permeation amount using the space portion 53 in the resin layer 51, it is unnecessary to excessively decrease the thickness of the inflatable portion 40 to increase the gas permeation amount. In addition, since the inflatable portion 40 includes the particulate portion 52 in the space portion 53, it is possible to increase the strength of the inflatable portion 40 while suppressing deformation of the space portion 53. In this way, it is possible to reduce the pressing force acting on the puncture site P over time without operation by a doctor or a nurse while favorably maintaining the strength of the inflatable portion 40.

In addition, the particulate portion 52 is made of the metallic material. In this way, an electrostatic repulsive force for repelling and dispersing the particles 52a can be relatively easily formed, and thus it is possible to easily manufacture the hemostatic device 10.

In addition, the particulate portion 52 includes the plurality of particles 52a, and the plurality of particles 52a forms a gap between adjacent particles 52a. Since gas can flow between the adjacent particles 52a, gas permeability in the particulate portion 52 can be improved. In this way, the gas in the inflatable portion 40 can be more favorably discharged.

In addition, the particulate portion 52 forms the uneven portion 51a in a part of the outer surface of the inflatable portion 40 in the state in which the inflatable portion 40 inflates. For this reason, the contact area between the outer surface of the inflatable portion 40 and the wrist W increases, and thus it is possible to favorably press the puncture site P by preventing shift of the inflatable portion 40 with respect to the puncture site P by an increase in friction.

In addition, the inflatable portion 40 has the marker 40c formed on the resin layer 51, and a distribution of the particulate portion 52 in the resin layer 51 at the position at which the marker 40c is formed and around the marker 40c (first region A1) is smaller than that in the other part (second region A2) of the resin layer 51. For this reason, it is possible to help ensure visibility of the puncture site P, and to rather easily perform positioning of the inflatable portion 40 with respect to the puncture site P using the marker 40c.

Modification 1

Figure 7:
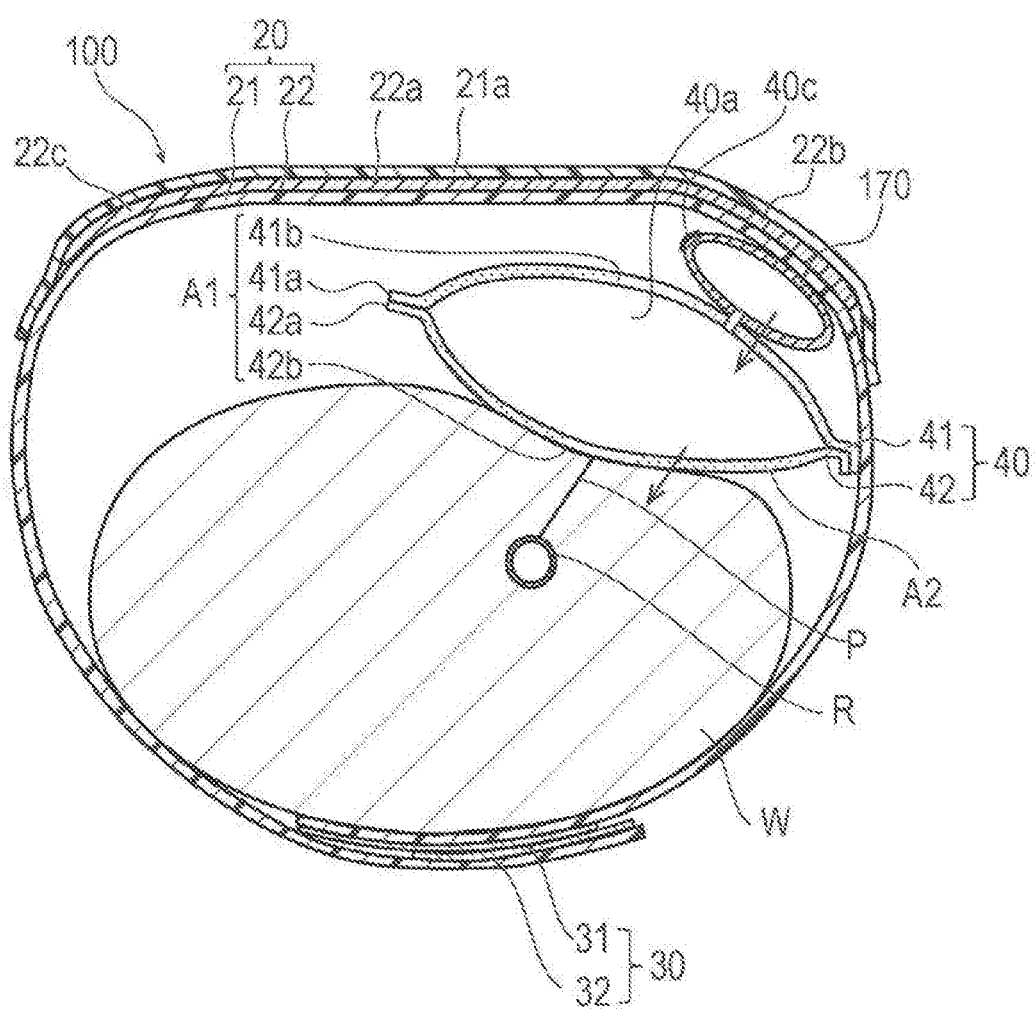
FIG. 7 is a cross-sectional view illustrating a hemostatic device according to Modification 1.

FIG. 7 is a diagram illustrating a hemostatic device 100 according to Modification 1. Hereinafter, the same reference symbol will be assigned to the same configuration as that of the embodiment, and a description of the reference symbols will be omitted.

The hemostatic device 100 according to Modification 1 is different from that of the embodiment in that an auxiliary pressing portion 170 is included between the inflatable portion 40 and the band 20 and the marker 40c is provided on the auxiliary pressing portion 170.

Similarly to the inflatable portion 40, the auxiliary pressing portion 170 is formed in a bag shape. The auxiliary pressing portion 170 is attached to the inflatable portion 40 such that an internal space of the auxiliary pressing portion 170 communicates with the inflatable space 40a of the inflatable portion 40. For this reason, when gas is injected into the inflatable portion 40, the auxiliary pressing portion 170 is inflated. Note that the auxiliary pressing portion 170 may be made of a sponge-like substance, an elastic material, an aggregate of fibers such as cotton, or, for example, a combination of one or more of a sponge-like substance, an elastic material, or an aggregate of fibers such as cotton.

The marker 40c is provided at an end portion of an outer surface of the auxiliary pressing portion 170 on a side close to a center of the inflatable portion 40. When such a marker 40c is provided on the auxiliary pressing portion 170, the inflatable portion 40 can be rather easily positioned with respect to the puncture site P, and thus position shift of the inflatable portion 40 is suppressed. In addition, since the marker 40c is provided on the auxiliary pressing portion 170, permeation of gas in the second region A2 of the inflatable portion 40 is not hindered. Note that a position at which the marker 40c is provided is not particularly limited as long as the inflatable portion 40 can be positioned in the puncture site P. For example, the marker 40c may be provided on the inflatable portion 40 side. In addition, the marker 40c may be provided on the belt 21 or the support plate 22 as long as the inflatable portion 40 can be positioned in the puncture site P.

According to the hemostatic device 100 according to Modification 1, as indicated by a solid arrow in FIG. 7, it is possible to adjust a direction of a pressing force applied by the inflatable portion 40 to a direction toward the puncture site P using the auxiliary pressing portion 170. In addition, since the auxiliary pressing portion 170 is provided, it is possible to ensure a relatively larger space between the second region A2 of the inflatable portion 40 and the band 20 when compared to the embodiment, and to increase an area of a portion which is exposed without coming into contact with the band 20 in the second region A2. For this reason, it is possible to more favorably discharge gas from this exposed portion.

Modification 2

Figure 8A:
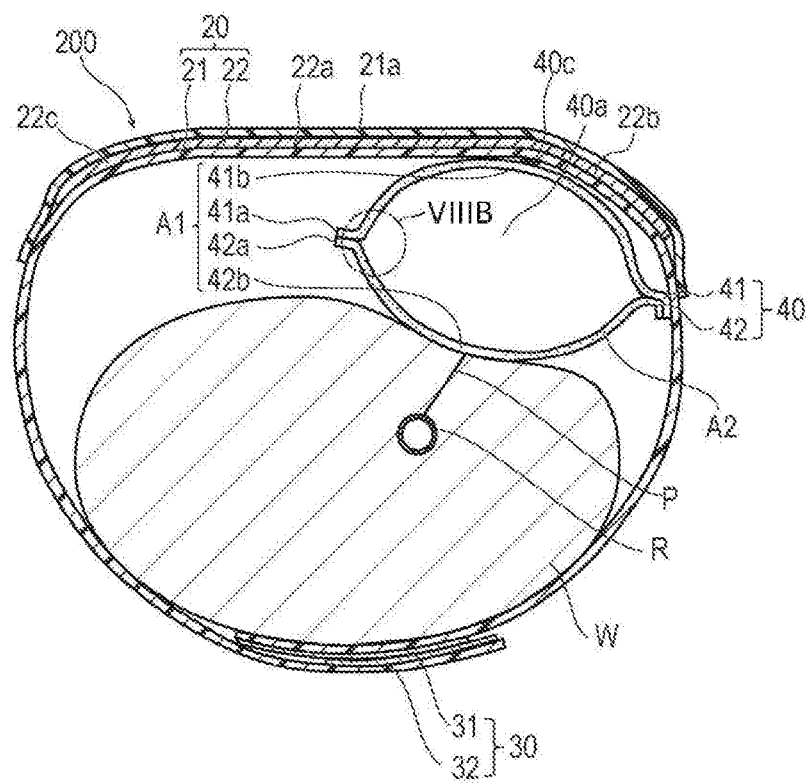
FIG. 8A is a cross-sectional view illustrating a hemostatic device according to Modification 2.
Figure 8B:
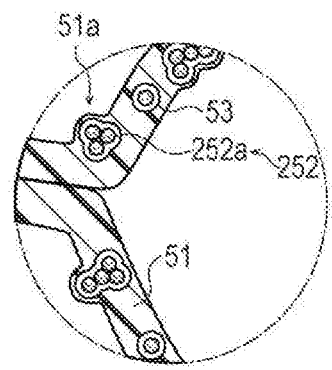
FIG. 8B is an enlarged cross-sectional view of a part VIIIB illustrated in FIG. 8A.

FIGS. 8A and 8B are diagrams illustrating a hemostatic device 200 according to Modification 2. Hereinafter, the same reference symbol will be assigned to the same configuration as that of the embodiment, and a description of the reference symbols will be omitted.

In the hemostatic device 200 according to Modification 2, a configuration of a particulate portion 252 included in the inflatable portion 40 is different from that of the embodiment.

The particulate portion 252 contains a porous particle 252a having a void. The porous particle 252a is not particularly limited. However, examples of the porous particle 252a can include zeolite. Note that the particulate portion 252 containing the porous particle 252a and a particulate portion not containing the porous particle 252a may be appropriately contained in the resin layer 51.

The particulate portion 252 of the hemostatic device 200 according to Modification 2 contains the porous particle 252a. For this reason, gas can flow into the porous particle 252a, and thus it is possible to further improve gas permeability. In this way, it is possible to more favorably discharge gas in the inflatable portion 40.

Even though the hemostatic device according to the disclosure has been described above through the embodiment and modifications, the disclosure is not limited only to the respective configurations described above, and can be appropriately changed based on the description of claims.

For example, each portion included in the hemostatic device may be replaced with a portion having an arbitrary configuration capable of exerting the same function. In addition, an arbitrary component may be added.

In addition, the disclosure is not limited to the hemostatic device used by being mounted on the wrist, and may be applied to a hemostatic device used by being mounted, for example, on a leg.

In addition, even though the inflatable portion includes two sheets in the embodiment, the inflatable portion is not particularly limited to this configuration as long as the inflatable portion includes the resin layer, the particulate portion, and the space portion and can be inflated by a gas. For example, the inflatable portion may include one sheet, and the sheet may be folded and formed in a bag shape by bonding or welding edge portions. Alternatively, the inflatable portion may include a balloon-shaped member not having an edge portion.

In addition, even though the second region is provided in each of two sheets, arrangement of the second region is not particularly limited as long as the gas in the inflatable portion can be discharged to the outside over time in a state in which the inflatable portion inflates.

The detailed description above describes a hemostatic device for performing hemostasis by pressing a punctured site. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
a band configured to be wrapped around a site where bleeding is to be stopped of a limb;
a fastener configured to secure the band to the limb in a wrapped state; and
an inflatable portion configured to be connected to the band and inflated with an inflation gas, wherein the inflatable portion includes a resin layer made of a resin material, a particulate portion dispersed in the resin layer, and a space portion formed around the particulate portion, and the space portion formed around the particulate portion configured to receive a gas, and wherein the gas is dispersed in the resin layer so as not to communicate between an inner surface of the resin layer and an outer surface of the resin layer, the inflatable portion including a first sheet of a resin material and a second sheet of a resin material, the first sheet being connected to the second sheet on an outer periphery of the first and the second sheets; and
a distribution of the particulate portion and the space portion in the resin layer of the first sheet in a central portion of the first sheet being less than a distribution of the particulate portion and the space portion in the resin layer in an other part of the resin layer of the first sheet, and a distribution of the particulate portion and the space portion in the resin layer of the second sheet in a central portion of the second sheet being less than a distribution of the particulate portion and the space portion in the resin layer in an other part of the resin layer of the second sheet.

2. The hemostatic device according to claim 1, wherein the particulate portion is made of a metallic material.

3. The hemostatic device according to claim 1, wherein the particulate portion includes a plurality of particles, and the plurality of particles forming a gap between the adjacent particles.

4. The hemostatic device according to claim 1, wherein the particulate portion forms an uneven portion on a part of an outer surface of the inflatable portion in a state in which the inflatable portion inflates.

5. The hemostatic device according to claim 1, wherein the particulate portion contains a porous particle.

6. The hemostatic device according to claim 1, wherein the inflatable portion has a marker on the central portion of the first sheet.

7. The hemostatic device according to claim 1, wherein the particulate portion has a substantially spherical shape.

8. The hemostatic device according to claim 1, wherein the band includes a support plate on which the inflatable portion is disposed and a belt on which the fastener is disposed, the support plate having a higher rigidity than that of the belt.

9. The hemostatic device according to claim 1, further comprising:
an auxiliary pressing portion arranged between the inflatable portion and the band.

10. The hemostatic device according to claim 1, wherein the space portion is configured to surround a portion of the particulate portion, and a part of the particulate portion is in contact with the resin layer.

11. The hemostatic device according to claim 1, wherein the first sheet and the second sheet each have a rectangular external shape.

12. The hemostatic device according to claim 1, further comprising:
an injection part disposed between a protrusion of the first sheet and a protrusion of the second sheet, the injection part configured to receive a tube connected to a source of the inflation gas.

13. The hemostatic device according to claim 1, wherein the resin material of the first sheet is a different material than the resin material of the second sheet.

14. A hemostatic device comprising:
a band configured to be wrapped around a site where bleeding is to be stopped of a limb;

a fastener configured to secure the band to the limb in a wrapped state;

an inflatable portion configured to be connected to the band and inflated with an inflation gas, wherein the inflatable portion includes a resin layer made of a resin material, a plurality of particulate portions dispersed in the resin layer, and a space portion formed around each of the plurality of particulate portions, the space portion formed around each of the plurality of particulate portions being configured to receive a gas; and wherein the inflatable portion has a marker formed on the resin layer, and a distribution of the plurality of particulate portions in the resin layer at a position at which the marker is formed and around the marker is smaller than the distribution of the plurality of particulate portions in an other part of the resin layer.

15. The hemostatic device according to claim 14, wherein each of the plurality of particulate portions is comprised of one or more spherical particles of a metallic material.

16. The hemostatic device according to claim 14, wherein the band includes a support plate on which the inflatable portion is disposed and a belt on which the fastener is disposed, the support plate having a higher rigidity than that of the belt.

17. The hemostatic device according to claim 14, further comprising:

an auxiliary pressing portion arranged between the inflatable portion and the band.

18. The hemostatic device according to claim 14, wherein the inflatable portion comprises:

a first sheet of a resin material and a second sheet of a resin material, and wherein the first sheet is connected to the second sheet on an outer periphery of the first and the second sheets, and an injection part disposed between a protrusion of the first sheet and a protrusion of the second sheet, the injection part configured to receive a tube connected to a source of the inflation gas.

19. A method for performing hemostasis on a puncture site of a blood vessel of a patient's limb, the method comprising:

wrapping a band of a hemostatic device around the patient's limb having the puncture site, the hemostatic device having an inflatable portion configured to be connected to the band and inflated with an inflation gas, wherein the inflatable portion includes a resin layer made of a resin material, a particulate portion dispersed in the resin layer, and a space portion formed around the particulate portion, and the space portion formed around the particulate portion configured to receive a gas, and wherein the gas is dispersed in the resin layer so as not to communicate between an inner surface of the resin layer and an outer surface of the resin layer;

positioning the inflatable portion over the puncture site using a marker formed on the resin layer, and wherein a distribution of the particulate portion in the resin layer at a position at which the marker is formed and around the marker is smaller than the distribution in an other part of the resin layer; and securing the band to the patient's limb in a wrapped state.

20. The method according to claim 19, further comprising:

inflating the inflatable portion with the gas to cause the inflation portion to apply a pressing force to the puncture site.

21. A hemostatic device comprising:

a band configured to be wrapped around a site where bleeding is to be stopped of a limb;

a fastener configured to secure the band to the limb in a wrapped state;

an inflatable portion configured to be connected to the band and inflated with an inflation gas, wherein the inflatable portion includes a resin layer made of a resin material, a particulate portion dispersed in the resin layer, and a space portion formed around the particulate portion, and the space portion formed around the particulate portion configured to receive a gas, and wherein the gas is dispersed in the resin layer so as not to communicate between an inner surface of the resin layer and an outer surface of the resin layer; and wherein the particulate portion forms an uneven portion on a part of an outer surface of the inflatable portion in a state in which the inflatable portion inflates.

* * * * *